MOUNTAIN ASH TREE
Filed Feb. 13, 1970 2 Sheets-Sheet 1
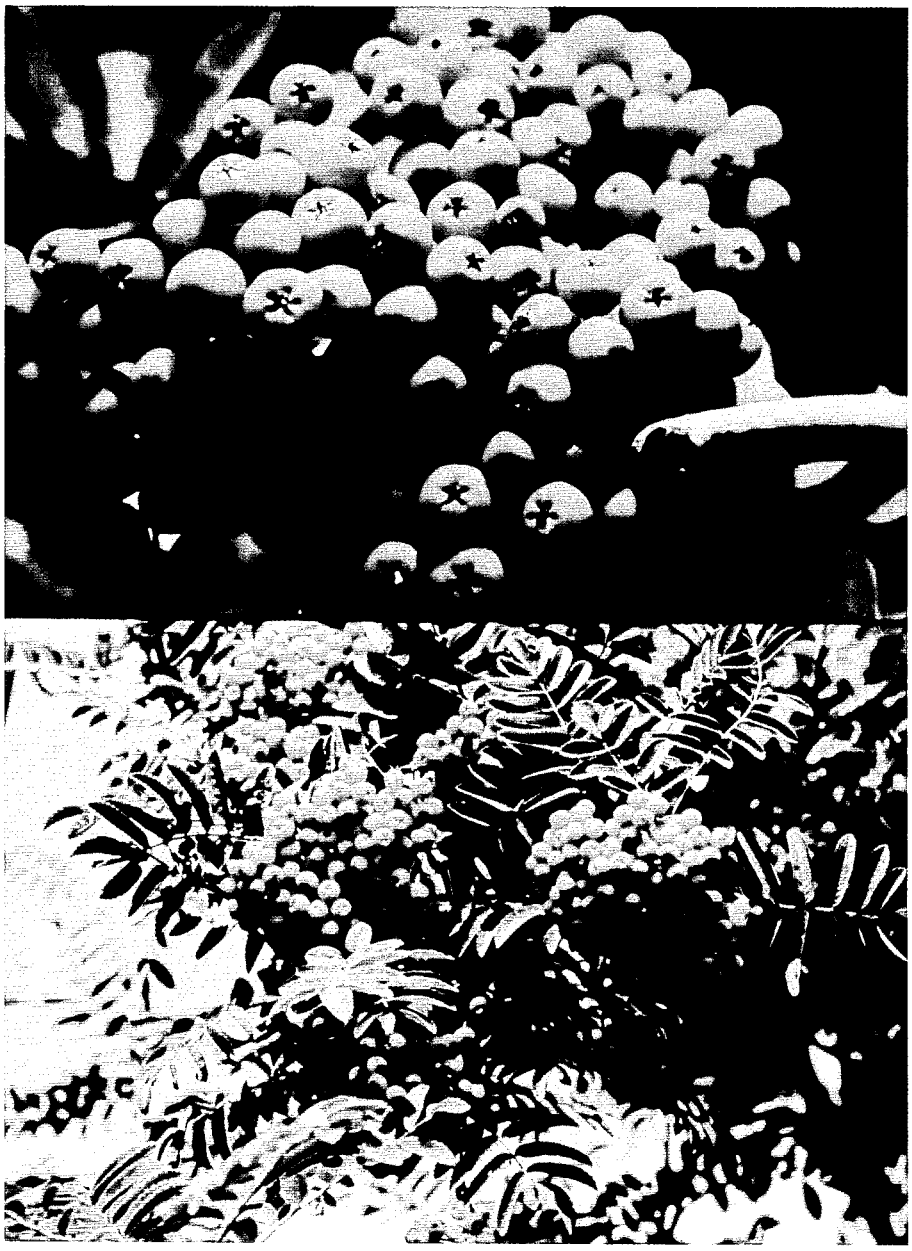
Inventor.
Milton Baron
By: Robb & Robb
Attorneys.

MOUNTAIN ASH TREE
Filed Feb. 13, 1970 2 Sheets-Sheet 2
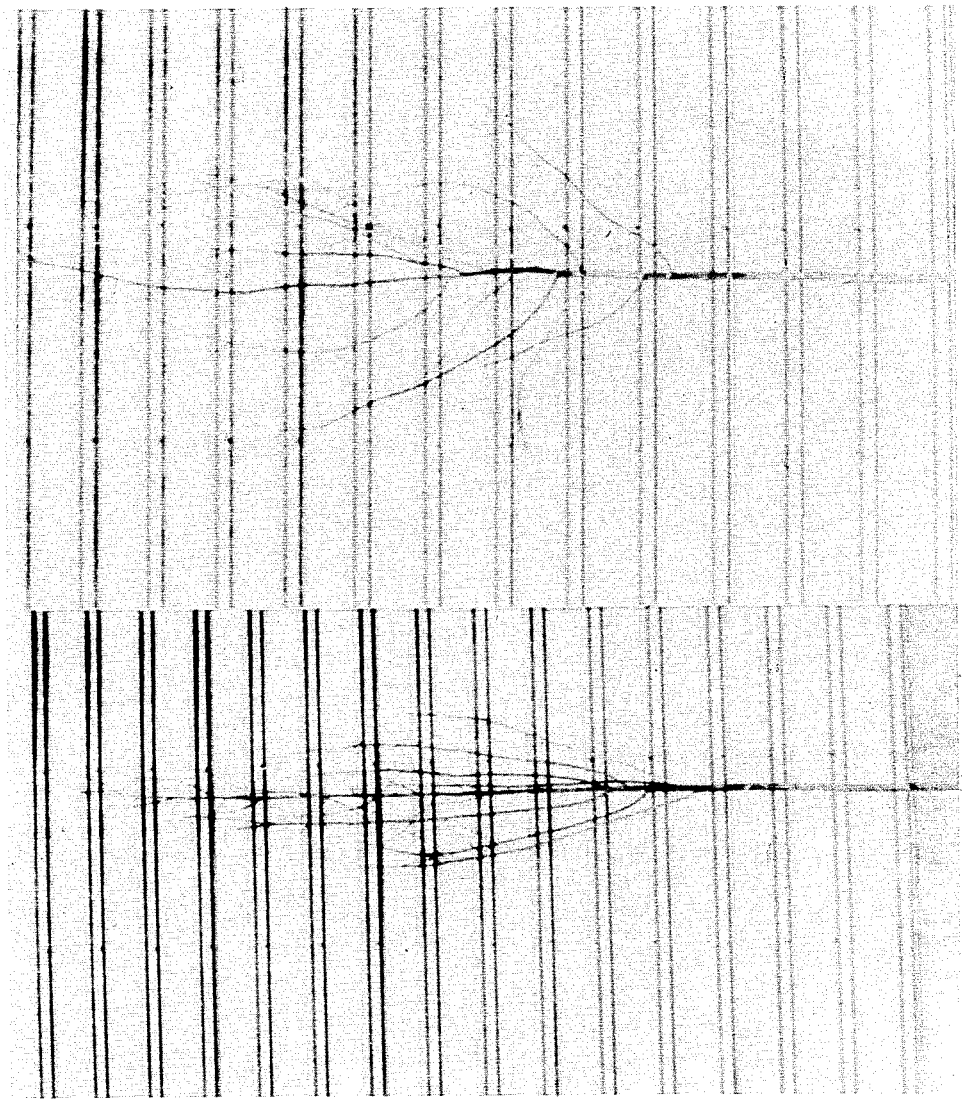
Inventor.
Milton Baron
By: Robb & Robb
Attorneys.

United States Patent Office

Plant Pat. 3,114

Patented Apr. 18, 1972

3,114

MOUNTAIN ASH TREE

Milton Baron, East Lansing, Mich., assignor to J. Frank Schmidt and Son Co., Troutdale, Oreg.

Filed Feb. 13, 1970, Ser. No. 11,359

Int. Cl. A01h *5/12*

U.S. Cl. Plt.—51 1 Claim

The present invention relates to a new and distinct variety of mountain ash tree of the European mountain ash species botanically known as *Sorbus aucuparia,* which was discovered by me as a selected cultivated seedling mutation of unknown parentage in a group of nursery plants of this species at East Lansing, Mich.

Among the nursery plants aforesaid which were being grown under my care and supervision, my attention was initially attracted to one particular young tree which bore fruit quite different from that of all other varieties of the *Sorbus aucuparia* species, as particularly evidenced by the deep rich red fruit color, with the fruit being borne in large, round and heavy clusters of highly ornamental appearance, and which are fully mature by mid-July in Michigan where the normal orange-red fruit typical of the species usually does not mature earlier than mid-August.

Continued observations and tests of the original seedling, and of progeny thereof asexually propagated therefrom on my behalf at Troutdale, Oreg., and Waynesboro, Pa., fully confirmed these distinctive features and convinced me that my new seedling is definitely a new and improved variety, as particularly evidenced by the following unique combination of the following primary characteristics which are outstanding therein and which distinguish the same from all other varieties of the European mountain ash species known to me:

(1) A heavier and straighter tree trunk structure;
(2) A better central leader which extends into the top of a medium dense tree crown which has an oval silhouette shape;
(3) A more vigorous and rapid habit of growth normally averaging 2 or more feet per year and with the capability of attaining a mature tree height of about 30 feet, while progeny trees derived from buddings produce whips or 6 or 7 feet tall in 1 year;
(4) The production of heavier, larger and more highly ornamental fruit clusters;
(5) An earlier fruit maturing habit, occurring by mid-July and which is at least 1 month earlier than is normal of the species when grown under the same conditions; and
(6) A distinctive and highly attractive deep rich red fruit color.

Asexual reproduction of my new variety, as performed by bubbing made on my behalf at Troutdale, Oreg., and at Waynesboro, Pa., shows that the foregoing characteristics and distinctions come true and are established and transmitted through succeeding propagations.

The accompanying drawings show a fragmentary portion of a typical tree of my new variety, depicting typical foliage and typical fruit clusters borne thereby, and also on a larger scale a typical mature specimen cluster of fruit, all as depicted in color as nearly true as it is reasonably possible to make the same in a color illustration of this character. The drawings also show (in black and white) views of a young tree specimen of my new variety and another variety of the same age which is typical of prior mountain ash species when grown under the same conditions, these views depicting their comparative tree structures and habits of growth.

The following is a detailed description of my new variety of mountain ash tree, with color terminology in accordance with the Horticultural Color Chart issued by the British Color Council in collaboration with the Royal Horticultural Society (vols. 1 and 2—copyright 1938, 1941), except where general color terms of ordinary dictionary significance are obvious:

Parentage: A selected seedling mutation of unknown parentage.

Propagation: Holds its distinguishing characteristics through succeeding propagations by bubbing.

Locality where grown and observed: East Lansing, Mich.

Tree: Small; upright; dense; hardly.

*Trunk.*—Stocky; smooth.

*Branches.* — Stocky; smooth. Color — Cordovan brown.

*Lenticels.*—Elliptical; sparse.

*Leaves.*—Pinnately compound of usually 19 leaflets in the average leaf.

Leaflets—Length—Average about 2; Width—Average from about ⅝ inch to ¾ inch; Shape—Ovate. Color—upper surface—Dark green; under surface—Pale green; Margin—Serrate; Petiole—medium length. Glands—highly variable in number ranging from none to 10 or more; occur on upper side of rachis at junctures of leaflet stalks; from papillate to filiform in shape. Color—Black. Stipules—Persistent; small; free tips from ⅛ inch to 3/16 inch long.

Flower buds:

*Hardiness.*—Fully hardy.

*Size.*—From ⅝ inch to ¾ inch long.

*Shape.*—Ovoid.

*Color.*—Dark purple brown.

Flowers: Typical of the species.

*Quantity.*—Abundant.

*Size.*—Small.

*Color.*—White.

*Petalage.*—Number of petals—5. Shape of petals—obovate. Size of petals—Length—3/16 inch. Width—⅛ inch.

Fruit: Pome, borne in heavy, highly ornamental, convex clusters averaging about 5½ inches in size and which usually mature by mid-July under normal conditions in Michigan.

*Quantity.*—Abundant; from about 140 to 160 fruit per cluster.

*Size.*—From ¼ inch to ⅜ inch.

*Color.*—Scarlet, Plate 19 at maturity; darkens with age to Signal Red, Plate 719 or Orient Red, Plate 819.

*Shape.*—Globose; fluted at the apex.

*Seeds.*—1 or 2 flattened elongated seeds contained in each of the 2 to 4 compartments.

*General observations*

The principal major differences between the new variety and others of the species are its heavier and earlier maturing fruit clusters and the rich red color of the fruit. In most other respects, the reproductive and vegetative parts are typical of the species. The exceptional vigor and form of the trees of the new variety, with their extremely straight trunks having good central leaders extending well into the oval tree crowns, contribute to special suitability of such trees to one-story residential developments, parks and street tree plantings.

I claim:

1. A new and distinct variety of mountain ash tree of the European mountain ash species botanically known as *Sorbus aucuparia,* substantially as herein shown and described, characterized particularly as to novelty by the unique combination of a heavier and straighter tree trunk structure, a better central leader which extends well into the top of a medium dense tree crown which has an oval silhouette shape, a more vigorous and rapid habit of growth normally averaging 2 or more feet per year and with a capability of attaining a mature tree height of about 30 feet, while progeny trees derived from buddings produce whips of 6 or 7 feet tall in 1 year, the production of heavier, larger and more highly ornamental fruit clusters, an earlier fruit maturing habit, occurring by mid- July and which is at least 1 month earlier than is normal of the species when grown under the same conditions, and a distinctive and highly attractive deep rich red fruit color.

No references cited.

ROBERT E. BAGWILL, Primary Examiner